US012059707B2

(12) United States Patent
Yazaki

(10) Patent No.: US 12,059,707 B2
(45) Date of Patent: Aug. 13, 2024

(54) ULTRASONIC PROBE AND ULTRASOUND DIAGNOSTIC APPARATUS

(71) Applicant: FUJIFILM Healthcare Corporation, Kashiwa (JP)

(72) Inventor: Toru Yazaki, Tokyo (JP)

(73) Assignee: FUJIFILM Healthcare Corporation, Chiba (JP)

( * ) Notice: Subject to any disclaimer, the term of this patent is extended or adjusted under 35 U.S.C. 154(b) by 36 days.

(21) Appl. No.: 17/728,091

(22) Filed: Apr. 25, 2022

(65) Prior Publication Data

US 2022/0355340 A1 Nov. 10, 2022

(30) Foreign Application Priority Data

Apr. 28, 2021 (JP) .................................. 2021-075878

(51) Int. Cl.
*B06B 1/02* (2006.01)
*A61B 8/00* (2006.01)

(52) U.S. Cl.
CPC .......... *B06B 1/0207* (2013.01); *A61B 8/4494* (2013.01); *A61B 8/461* (2013.01); *A61B 8/54* (2013.01); *A61B 8/56* (2013.01)

(58) Field of Classification Search
CPC ..... B06B 1/0207; A61B 8/4494; A61B 8/461; A61B 8/54; A61B 8/56; A61B 8/5207
See application file for complete search history.

(56) References Cited

U.S. PATENT DOCUMENTS 5,909,187 A * 6/1999 Ahuja ............... H03K 17/04106
341/135
2006/0279345 A1* 12/2006 Koo ..................... H04L 25/0278
327/308

(Continued)

FOREIGN PATENT DOCUMENTS

JP H11-290321 A 10/1999
JP 2006-345494 A 12/2006

(Continued)

OTHER PUBLICATIONS

Japanese official action dated Nov. 7, 2023 (and machine translation thereof) in connection with corresponding Japanese Patent Application No. 2021-075878.

*Primary Examiner* — Alexei Bykhovski
(74) *Attorney, Agent, or Firm* — Paul Teng

(57) ABSTRACT

An ultrasound diagnostic apparatus and an ultrasonic probe are provided which are capable of reducing a leak current even in combined use of a low voltage transmission circuit and a high voltage transmission circuit including a buffer. The ultrasonic probe includes: a high voltage transmission circuit for transmitting a relatively high voltage; a low voltage transmission circuit for transmitting a relatively low voltage; and a transducer for selectively receiving a voltage transmitted from the high voltage transmission circuit and the low voltage transmission circuit. The high voltage transmission circuit includes: a current source for varying a current generated thereby and a current drawn thereby based on a set signal; a buffer for driving the transducer in accordance with the currents generated and drawn by the current source; and an impedance controller connected to an input terminal and an output terminal of the buffer.

6 Claims, 6 Drawing Sheets

(56) References Cited

U.S. PATENT DOCUMENTS

| | | | | |
|---|---|---|---|---|
| 2011/0245677 A1* | 10/2011 | Sato | ................... | A61B 8/54 |
| | | | | 600/447 |
| 2017/0370886 A1* | 12/2017 | Nishimoto | ............. | G01N 29/30 |
| 2018/0035974 A1* | 2/2018 | Kajiyama | ............... | H04B 17/29 |
| 2018/0271493 A1* | 9/2018 | Jensen | ................. | B06B 1/0215 |
| 2018/0287399 A1* | 10/2018 | Yamaguchi | ........... | H02J 7/0029 |
| 2020/0163652 A1* | 5/2020 | Kajiyama | ............ | A61B 8/5207 |

FOREIGN PATENT DOCUMENTS

| | | |
|---|---|---|
| JP | 2007-244687 A | 9/2007 |
| JP | 6309093 | 4/2018 |
| WO | WO2015-186234 A1 | 12/2015 |

\* cited by examiner

ULTRASONIC PROBE AND ULTRASOUND DIAGNOSTIC APPARATUS

CLAIM OF PRIORITY

The present application claims priority from Japanese Patent Application JP 2021-075878 filed on Apr. 28, 2021, the content of which is hereby incorporated by reference into this application.

BACKGROUND OF THE INVENTION

The present invention relates to a medical ultrasonic probe and a medical ultrasound diagnostic apparatus and, more particularly, to a transmission circuit for driving each transducer of an ultrasonic probe.

An ultrasound diagnostic apparatus receives an echo signal of ultrasonic waves transmitted to an object under examination to take a tomographic image of the object under examination and/or a doppler image that represents an imaged blood flow distribution. Each transducer of an ultrasonic probe for transmitting ultrasonic waves is applied with a relatively high voltage on the order of 100 V when capturing the tomographic image, whereas each transducer is continuously applied with a relatively low voltage on the order to several V when capturing the doppler image. Also, for improving a spatial resolution of a tomographic image or doppler image, it is required to reduce the size of each transducer as well as an amplifier circuit for applying a voltage to each transducer to individually drive it.

For reducing an amplifier circuit in size, Japanese Patent No. 6309093, for example, discloses an amplifier circuit and an ultrasonic probe. The amplifier includes a current source for changing currents generated and drawn thereby based on a set signal, and a buffer for driving transducers in accordance with the currents generated and drawn by the current source.

However, if the amplifier circuit in the above Patent No. 6309093 is of a high voltage transmission circuit for imaging a tomographic image and a low voltage transmission circuit for imaging a doppler image is installed separately from the high voltage transmission circuit, a leak current may occur in the buffer. Specifically, due to a relatively low output impedance of the high voltage transmission circuit including the buffer, a leak current may occur with respect to a signal transmitted from the low voltage transmission circuit.

SUMMARY OF THE INVENTION

It is accordingly an object of the present invention to provide an ultrasound diagnostic apparatus and an ultrasonic probe capable of reducing the leak current even in combined use of a low voltage transmission circuit and a high voltage transmission circuit including a buffer.

To achieve the above object, an aspect of the present invention provides an ultrasonic probe including: a high voltage transmission circuit for transmitting a relatively high voltage; a low voltage transmission circuit for transmitting a relatively low voltage; and a transducer for selectively receiving a voltage transmitted from the high voltage transmission circuit and the low voltage transmission circuit. The high voltage transmission circuit includes: a current source for varying a current generated thereby and a current drawn thereby based on a set signal; a buffer for driving the transducer in accordance with the currents generated and drawn by the current source; and an impedance controller connected to an input terminal and an output terminal of the buffer.

Further, another aspect of the present invention provides an ultrasound diagnostic apparatus including the ultrasonic probe.

According to the present invention, an ultrasound diagnostic apparatus and an ultrasonic probe are provided which are capable of reducing the leak current even in combined use of a low voltage transmission circuit and a high voltage transmission circuit including a buffer.

DETAILED DESCRIPTION OF THE PREFERRED EMBODIMENTS

Embodiments of the ultrasound diagnostic apparatus and the ultrasonic probe according to the present invention will be described with reference to the accompanying drawings. Throughout the drawings for describing the embodiments, like reference signs are used to indicate like components in principle and a repeated description is omitted.

If necessary for convenience's sake, the description will be given in a plurality of sections or embodiments and, unless expressly stated otherwise, they are not independent of one another, one of them corresponding to an example modification, details, and/or a supplementary description of all or part of another one, and the like. Also, in the following embodiments, whenever a reference is made to the number (including piece counts, numeric values, amount, ranges and the like) of elements, unless expressly stated otherwise, unless clearly limited to a specific number in principle, and the like, the number of elements is not limited to a specific number, and may be equal to or greater or equal to or less than the specific number.

Furthermore, in the following embodiments, unless expressly stated otherwise, unless clearly considered to be essential in principle, and the like, the component elements (including elemental steps and the like) of the embodiments should be not necessarily essential. Similarly, in the following embodiments, unless expressly stated otherwise, unless clearly considered otherwise in principle, and the like, whenever reference is made to a shape, positional relationship and the like of component elements and the like, it is understood to include substantial approximations or analogs to the shape and the like. The same is applied to the numeric values and ranges described above.

Figure 1:
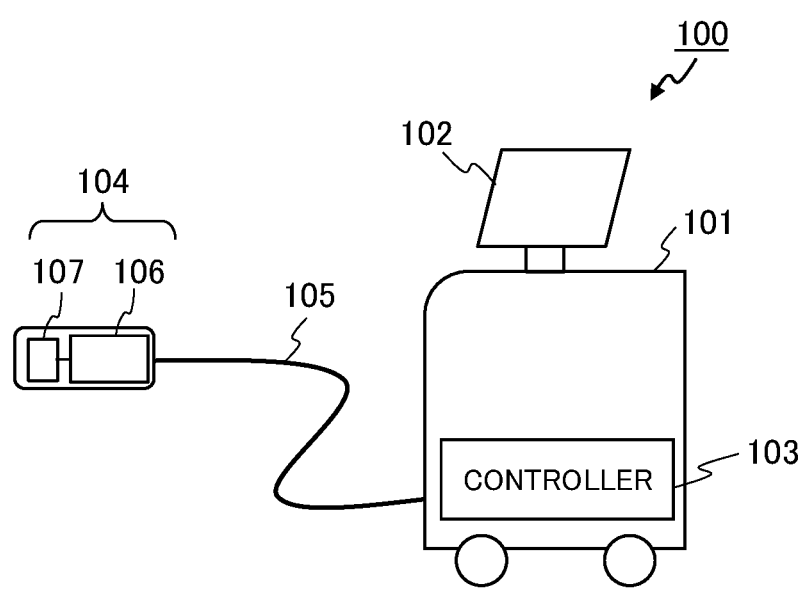
FIG. 1 is an overall configuration diagram of an ultrasound diagnostic apparatus according to the present invention.

An example of an ultrasound diagnostic apparatus 100 according to the present invention is described with reference to FIG. 1. The ultrasound diagnostic apparatus 100 receives an echo signal of ultrasonic waves transmitted to an object under examination and thereby obtains a tomographic image of the object under examination and/or a doppler image representing an imaged blood flow distribution. The ultrasound diagnostic apparatus 100 includes an ultrasonic probe 104 and a main body 101 which are electrically interconnected through a cable 105.

The ultrasonic probe 104 transmits ultrasonic waves to the object under examination and receives an echo signal from the object under examination, and has a transducer unit 107 and a control IC (Integrated Circuit) 106. The control IC 106 is implemented, for example, by a single semiconductor chip. The configuration of the ultrasonic probe 104 will be described later in detail with reference to FIG. 2.

The main body 101 provides power for the ultrasonic probe 104 for transmitting ultrasonic waves, and generates and displays a tomographic image and a doppler image based on an echo signal received by the ultrasonic probe 104. The main body 101 includes a controller 103 and a display 102. The controller 103, which includes a CPU (Central Processor Unit), a DSP (Digital Signal processor), a storage device, a communication interface, a user interface and the like, controls power provided to the ultrasonic probe, and generates a tomographic image and the like based on an echo signal. The display 102, for example, a liquid crystal display, displays a tomographic image and the like generated by the controller 103. Imaging conditions for a tomographic image and the like are set by an operator through a user interface such as a keyboard, a mouse, a touch panel displayed on the display 102, and the like.

Figure 2:
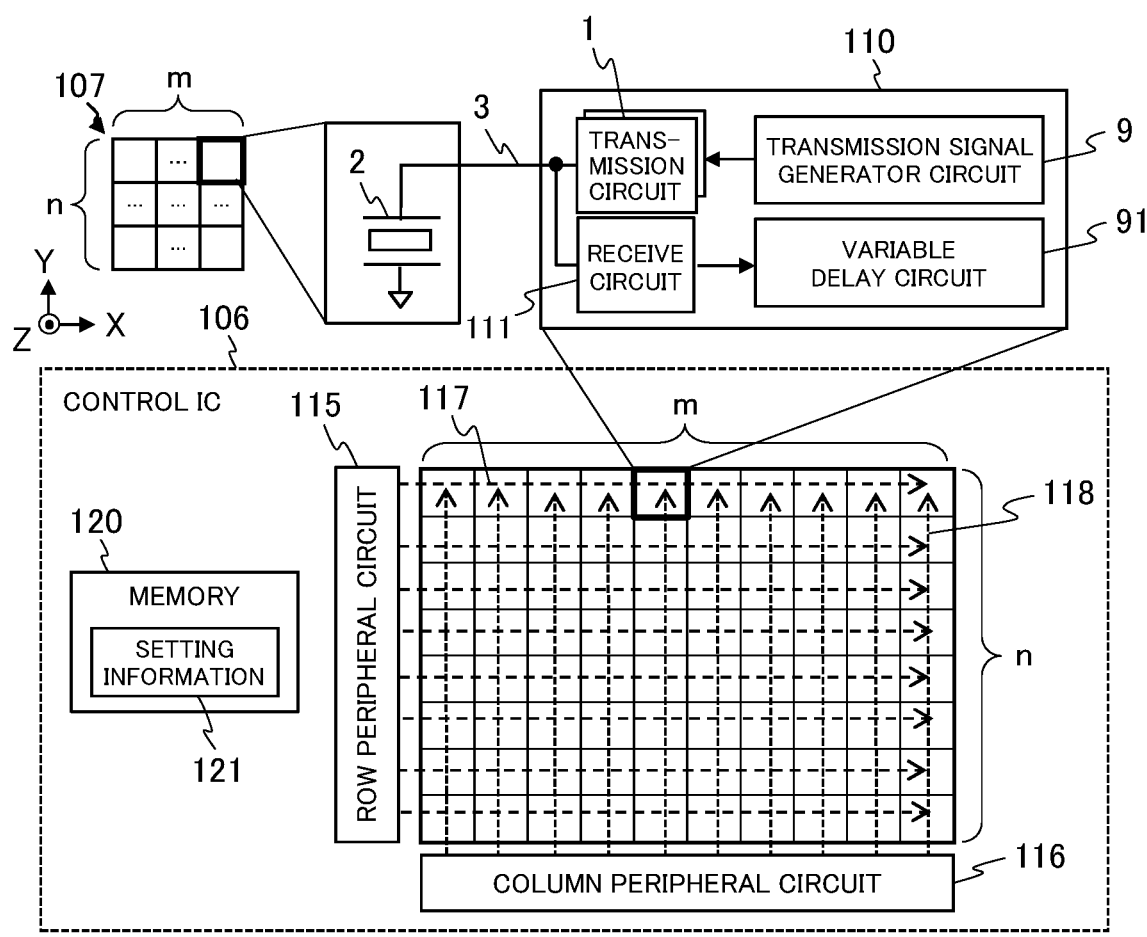
FIG. 2 is a configuration diagram of an ultrasonic probe according to the present invention.

An example of the ultrasonic probe 104 is described with reference to FIG. 2. As described above, the ultrasonic probe 104 has the transducer unit 107 and the control IC 106. The transducer unit 107 has a plurality of transducers 2 which transmit ultrasonic waves to the object under examination and receive echo signals from the object under examination. The transducers 2 are arranged, for example, in a two-dimensional array with n rows and m columns where m transducers are arranged in the X direction which is the row direction and n transducers are arranged in the Y direction which is the column direction.

The control IC 106 has a plurality of transducer control units 110, a row peripheral circuit 115, a column peripheral circuit 116 and memory 120. The transducer control units 110 are electrically connected to the respective transducers 2 through wirings 3 on an individual basis. Each transducer control unit 110 has a transmission circuit, 1, a transmission signal generator circuit 9, a receive circuit 111 and a variable delay circuit 91.

The transmission circuit 1 applies a voltage to the transducer 2 to drive the transducer 2 to transmit ultrasonic waves, and controls the voltage to be applied to the transducer 2 according to an image to be captured. For example, a relatively high voltage on the order of 100 V is applied to capture a tomographic image, and a relatively low voltage on the order to several V is continuously applied to capture a doppler image. A detailed configuration of the transmission circuit 1 will be described later with reference to FIG. 3.

The transmission signal generator circuit 9 controls timing at which the transmission circuit 1 drives the transducer 2. For example, the transmission signal generator circuit 9 controls timing so as to scan a point at which the ultrasonic waves transmitted from the plurality of transducers 2 are superimposed within the object under examination.

The receive circuit 111 amplifies an echo signal received by the transducer 2. The variable delay circuit 91 sets a delay time on an echo signal depending on the distance to each transducer 2 from the point at which the ultrasonic waves transmitted to the object under examination are superimposed. The echo signal on which the delay time is set is transmitted to the controller 103 for use in generation of a tomographic image and the like.

The row peripheral circuit 115 controls the individual transducer control units 110 in rows by n sets of row control signals 117. The column peripheral circuit 116 controls the individual transducer control units 110 in columns by m sets of column control signals 118. The row control signals 117 and the column control signals 118 include setting signals such as a signal for selecting a specific transducer 2, a signal for defining a delay time for the individual transducer 2, and the like, and are stored in the memory 120 as setting information 121.

Figure 3:
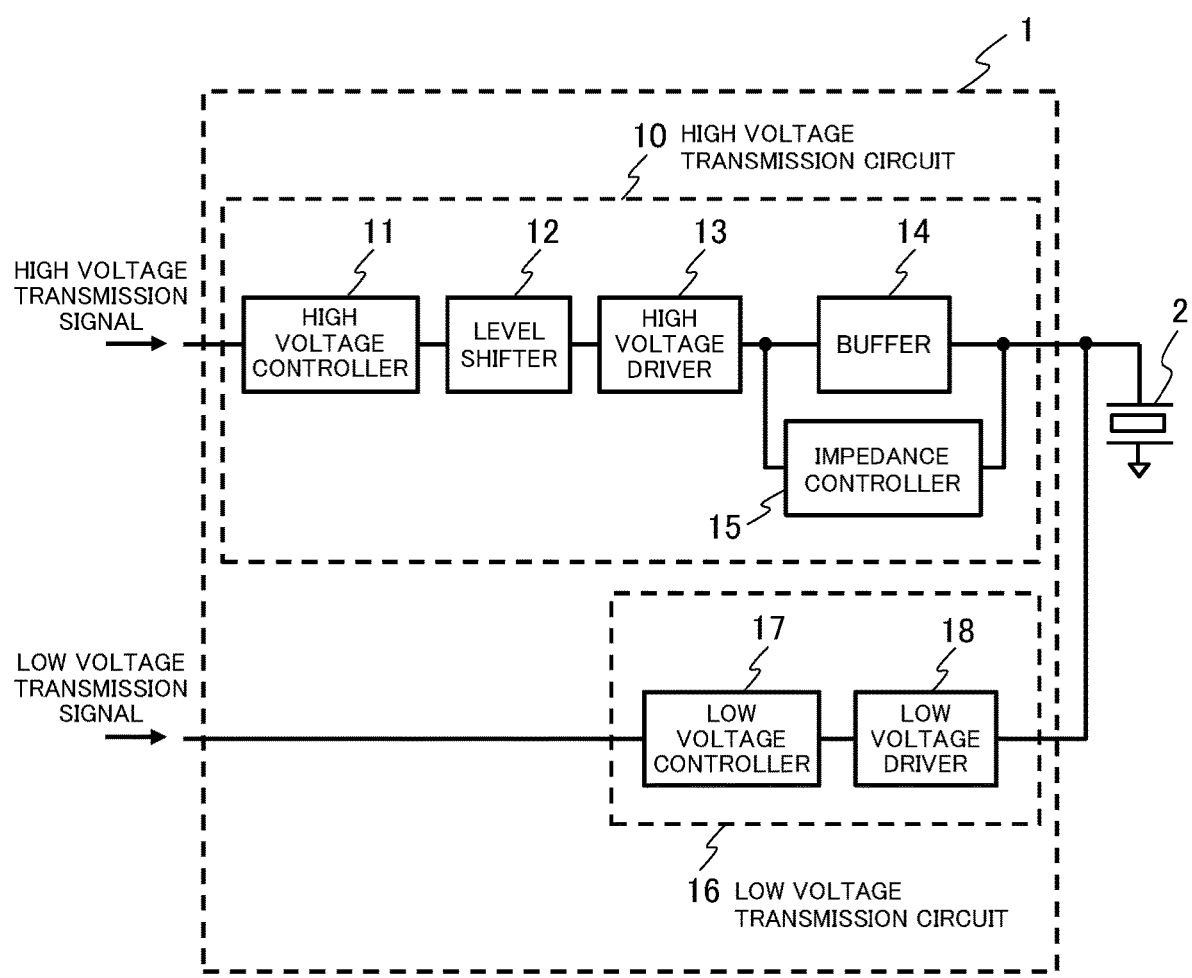
FIG. 3 is a configuration diagram of a transmission circuit of the ultrasonic probe according to the present invention.

An example of the transmission circuit 1 is described with reference to FIG. 3. The transmission circuit 1 has a high voltage transmission circuit 10 and a low voltage transmission circuit 16, and selectively operates any one of the high voltage transmission circuit 10 and the low voltage transmission circuit 16 depending on an image to be captured.

The high voltage transmission circuit 10, which operates to apply a relatively high voltage to the transducer 2 when capturing a tomographic image, has a high voltage controller 11, a level shifter 12, a high voltage driver 13, a buffer 14, and an impedance controller 15. The high voltage controller 11 is controlled in accordance with a high voltage transmission signal transmitted from the transmission signal generator circuit 9, to generate a signal to be transmitted to the level shifter 12. The level shifter 12 converts a voltage level of the signal transmitted from the high voltage controller 11. The high voltage driver 13 outputs the signal having its voltage level converted by the level shifter 12, to the transducer 2 through the buffer 14.

The low voltage transmission circuit 16, which operates to apply a relatively low voltage to the transducer 2 when capturing a doppler image, has a low voltage controller 17 and a low voltage driver 18. The low voltage controller 17 generates a signal to be transmitted to the low voltage driver 18 in accordance with a low voltage transmission signal transmitted from the transmission signal generator circuit 9. The low voltage driver 18 outputs, to the transducer 2, the signal transmitted from the low voltage controller 17.

As described above, the high voltage transmission circuit 10 and the low voltage transmission circuit 16 are connected to the transducer 2. A relatively low output impedance of the high voltage transmission circuit 10 including the buffer 14 may cause a leak current to occur in the buffer 14 due to a signal transmitted from the low voltage transmission circuit 16. To address this, the high voltage transmission circuit 10 in FIG. 3 includes an impedance controller 15 connected to an input terminal and an output terminal of the buffer 14. Installing the impedance controller 15 in the high voltage transmission circuit 10 reduces a leak current in the buffer 14 in which the input and the output become at the same potential. The high voltage controller 11, the level shifter 12, and the high voltage driver 13 function as a variable current source that varies a current generated thereby and a current drawn thereby based on a set signal.

Figure 4:
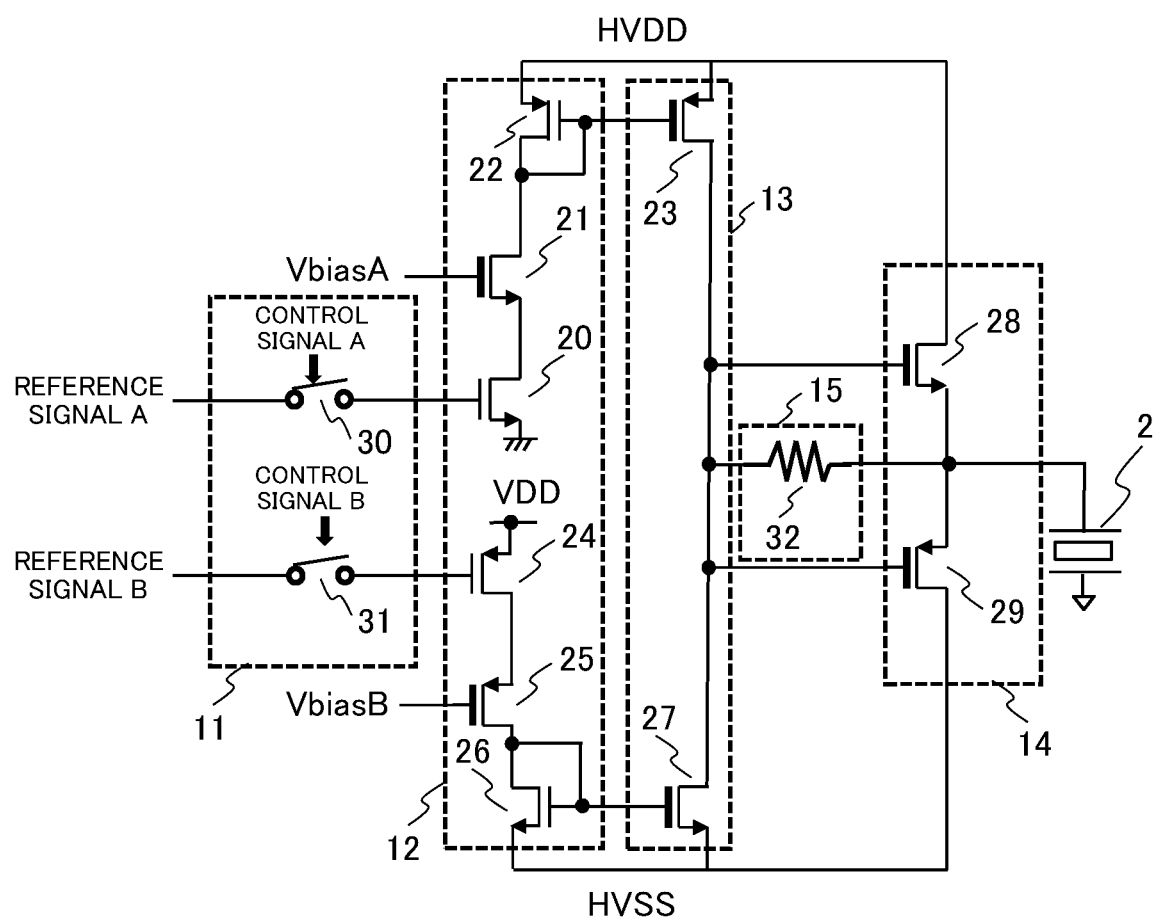
FIG. 4 is a diagram of a specific example of a high voltage transmission circuit in the transmission circuit.

Reference is made to FIG. 4 for a description of a specific example of the high voltage transmission circuit 10 having the high voltage controller 11, the level shifter 12, the high voltage driver 13, the buffer 14, and the impedance controller 15.

The high voltage controller 11 has a switch 30 and a switch 31. The switch 30 has one end at which a reference signal A is received, and the other end connected to a gate terminal of an N-type MOS transistor 20 of the level shifter 12. The switch 31 has one end at which a reference signal B is received, and the other end connected to a gate terminal of a P-type MOS transistor 24 of the level shifter 12. The reference signal A and the reference signal B are, for example, 1V and VDD-1V. The switch 30 and the switch 31 are respectively controlled to be turned ON/OFF by a control signal A and a control signal B which are high voltage transmission signals transmitted from the transmission signal generator circuit 9.

The level shifter 12 has an N-type MOS transistor 20, an N-type high voltage MOS transistor 21, a P-type MOS transistor 22, a P-type MOS transistor 24, a P-type high voltage MOS transistor 25, and an N-type MOS transistor 26.

The N-type MOS transistor 20 has a gate terminal connected to the switch 30, a source terminal connected to a ground potential, and a drain terminal connected to a source terminal of the N-type high voltage MOS transistor 21. The N-type high voltage MOS transistor 21 has a gate terminal applied with a bias voltage VbiasA, the source terminal connected to the drain terminal of the N-type MOS transistor 20, and a drain terminal connected to a drain terminal and a gate terminal of the P-type MOS transistor 22. The P-type MOS transistor 22 has the drain terminal and the gate terminal that are connected to the drain terminal of the N-type high voltage MOS transistor 21, and a source terminal connected to HVDD which is high voltage positive wiring.

The P-type MOS transistor 24 has a gate terminal connected to the switch 31, a source terminal connected to VDD which is low voltage positive side wiring, and a drain terminal connected to a source terminal of the P-type high voltage MOS transistor 25. The P-type high voltage MOS transistor 25 has a gate terminal applied with a bias voltage VbiasB, the source terminal connected to the drain terminal of the P-type MOS transistor 24, and a drain terminal connected to a drain terminal and a gate terminal of the N-type MOS transistor 26. The N-type MOS transistor 26 has the drain terminal and the gate terminal that are connected to the drain terminal of the P-type high voltage MOS transistor 25, and a source terminal connected to HVSS which is high voltage negative wiring.

Upon the control signal A turning on the switch 30, the reference signal A is applied to the gate terminal of the N-type MOS transistor 20, so that a current according to the reference signal A flows from the drain terminal of the N-type MOS transistor 20. When the current flows from the drain terminal of the N-type MOS transistor 20, a signal having its voltage level converted from that of the control signal A is transmitted to the P-type MOS transistor 22 via the N-type high voltage MOS transistor 21. Stated another way, the N-type MOS transistor 20, the N-type high voltage MOS transistor 21, and the P-type MOS transistor 22 function as the level shifter 12 to convert the voltage level of the control signal A for ON/OFF control on the switch 30. Likewise, the P-type MOS transistor 24, the P-type high voltage MOS transistor 25, and the N-type MOS transistor 26 function as the level shifter 12 to convert the voltage level of the control signal B for ON/OFF control on the switch 31.

The high voltage driver 13 has a P-type high voltage MOS transistor 23 and an N-type high voltage MOS transistor 27. The P-type high voltage MOS transistor 23 has a gate terminal applied with a signal having its voltage level converted from that of the control signal A, a source terminal connected to HVDD, and a drain terminal connected to a gate terminal of an N-type high voltage MOS transistor 28 of the buffer 14. The N-type high voltage MOS transistor 27 has a gate terminal applied with a signal having its voltage level converted from that of the control signal B, a source terminal connected to HVSS, and a drain terminal connected to a gate terminal of a P-type high voltage MOS transistor 29 of the buffer 14.

Upon the gate terminal of the P-type high voltage MOS transistor 23 being applied with a signal having its voltage level converted from that of the control signal A, a current according to the voltage applied to the gate terminal flows from the drain terminal. Stated another way, the P-type high voltage MOS transistor 23 functions as the high voltage driver 13 to output a signal having its voltage level converted. Likewise, the N-type high voltage MOS transistor 27 functions as the high voltage driver 13 to output a signal having its voltage level converted.

The buffer 14 has the N-type high voltage MOS transistor 28 and the P-type high voltage MOS transistor 29. The N-type high voltage MOS transistor 28 has the gate terminal connected to the drain terminal of the P-type high voltage MOS transistor 23, a drain terminal connected to HVDD, and a source terminal connected to the transducer 2. The P-type high voltage MOS transistor 29 has the gate terminal connected to the drain terminal of the N-type high voltage MOS transistor 27, a drain terminal connected to HVSS, and a source terminal connected to the transducer 2. Stated another way, the source terminals of the N-type high voltage MOS transistor 28 and the P-type high voltage MOS transistor 29 serve as an output terminal of the buffer 14. Also, the gate terminal of the N-type high voltage MOS transistor 28 and the gate terminal of the P-type high voltage MOS transistor 29 are connected and serve as an input terminal of the buffer 14.

The currents flowing from the drain terminals of the P-type high voltage MOS transistor 23 and the N-type high voltage MOS transistor 27 of the high voltage driver 13 cause an increase in voltage at the gate terminals of the N-type high voltage MOS transistor 28 and the P-type high voltage MOS transistor 29. Upon an increase in voltage at the gate terminals, voltages at a level equal to that of the increased voltage are output from the source terminals of the N-type high voltage MOS transistor 28 and the P-type high voltage MOS transistor 29, so that the transducer 2 is operated by the voltages output from the source terminals. Stated another way, the N-type high voltage MOS transistor 28 and the P-type high voltage MOS transistor 29 function as the buffer 14 to drive the transducer 2 in accordance with the current generated or drawn by the current source having the high voltage controller 11, the level shifter 12, and the high voltage driver 13.

The impedance controller 15 includes a resistance 32 connected parallel to the buffer 14, for example. In the transmission circuit 1 illustrated in FIG. 4, when the transducer 2 is driven through the low voltage transmission circuit 16, the voltage from the low voltage transmission circuit 16 is also applied to the transducer 2 as well as the output end of the high voltage transmission circuit 10. Nevertheless, during the operation of the low transmission circuit 16, the high voltage transmission circuit 10 is at rest with the high voltage driver 13 in the off state. Therefore, the resistance 32 causes a transient voltage change at the input terminal of the buffer 14 to be at the same potential as at the output terminal thereof. As a result, the gate to source voltages of the N-type high voltage MOS transistor 28 and the P-type high voltage MOS transistor 29 are at the same potential. This results in a reduction in a leak current occurring in the buffer 14. It is desirable that the resistance value of the resistance 32 is sufficiently lower than the output impedance of the high voltage driver 13 and is in a similar level to the drain to source resistances of the N-type high voltage MOS transistor 28 and the P-type high voltage MOS transistor 29.

An appropriate range of resistance values Rzctl of the resistance 32 can be determined from two constraint conditions. The first one of the two constraint conditions is to prevent the resistance 32 from interfering with the transducer 2 driven by the buffer 14 of the high voltage transmission circuit 10, that is, to bring an amplification factor An closer to 1, the amplification factor An being a ratio of an input signal Vin to an output signal Vout of the buffer 14. The amplification factor An of the buffer 14 is expressed by the following equation.

$$An = \frac{Vout}{Vin} = \frac{gm \cdot ro + \frac{ro}{Rzctl}}{1 + gm \cdot ro + \frac{ro}{Rzctl}} \quad \text{(Eq. 1)}$$

Here gm is a transconductance coefficient of the N-type high voltage MOS transistor 28 and the P-type high voltage MOS transistor 29, and ro is an output resistance of the N-type high voltage MOS transistor 28 and the P-type high voltage MOS transistor 29. It is noted that the transconductance coefficients of the N-type high voltage MOS transistor 28 and the P-type high voltage MOS transistor 29 have the same value. The output resistances of the N-type high voltage MOS transistor 28 and the P-type high voltage MOS transistor 29 also have the same value.

In a typical semiconductor process, gm·ro>1. Because of this, Rzctl may be in a level similar to or greater than ro for the purpose of bringing the amplification factor An closer to one. In short, Rzctl≥ro is the first one of the constraint conditions.

The second one of the constraint conditions is to eliminate a potential difference between the output and the input of the buffer 14 when a signal is applied from the output of the high voltage transmission circuit 10. When the output impedance of the high voltage driver 13 is Zout, the relationship between the input signal Vin and the output signal Vout of the buffer 14 is expressed by the following equation.

$$\frac{Vin}{Vout} = \frac{Zout}{Zout + Rzctl} \quad \text{(Eq. 2)}$$

In the above equation, to satisfy Vin/Vout=1, Zout>>Rzctl should be established. This is the second one of the constraint conditions. Thus, from the two constraint conditions, the appropriate range of resistance values Rzctl of the resistance 32 is ro≤Rzctl<<Zout. When the resistance value Rzctl is in the appropriate range, the operation of the high voltage transmission circuit 10 is not obstructed, so that the leak current can be reduced in the buffer 14.

Figure 5:
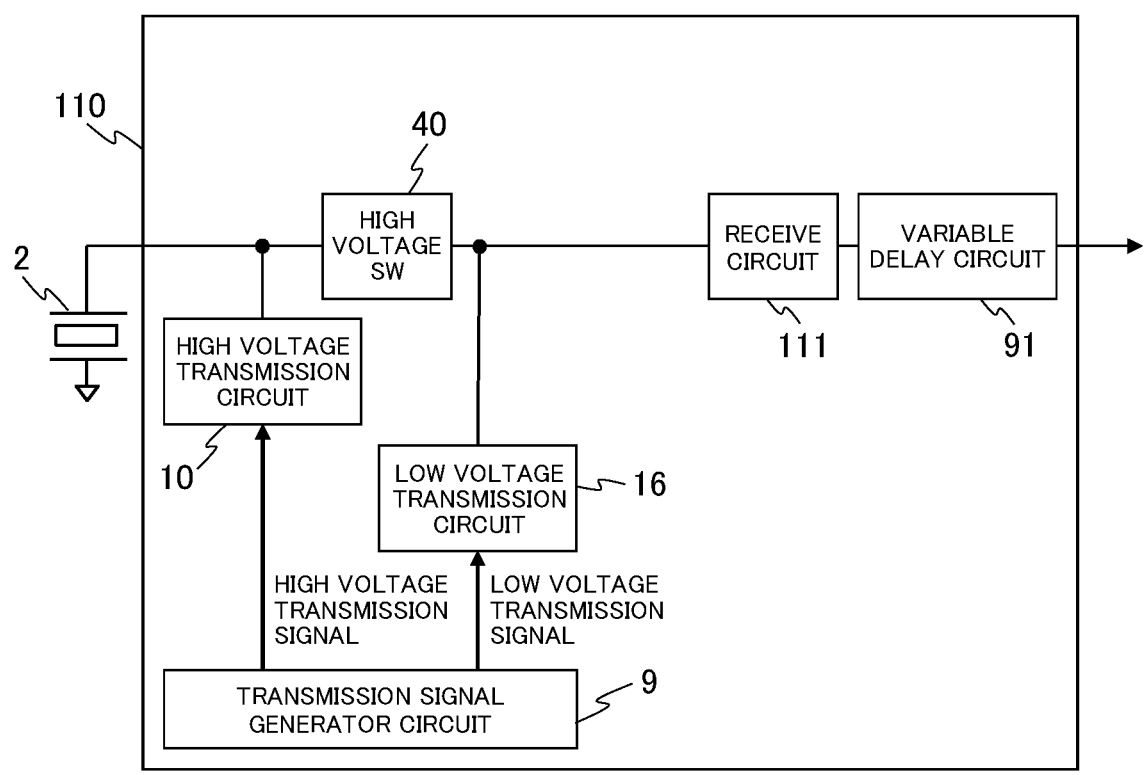
FIG. 5 is a diagram illustrating an example layout in a transducer control unit.

With reference to FIG. 5, an example layout in the transducer control unit 110 is described. In FIG. 5, a high voltage switch 40 is disposed between the transducer 2 and the low voltage transmission circuit 16 and the receive circuit 111. The high voltage switch 40 is on off controlled based on the operation of the high voltage transmission circuit 10 or the low voltage transmission circuit 16. Specifically, the high voltage switch 40 turns off during the operation of the high voltage transmission circuit 10, and turns on during the operation of the low voltage transmission circuit 16. By such on off control, the low voltage transmission circuit 16 and the receive circuit 111 can be prevented from is broken down by a relatively high voltage output from the high voltage transmission circuit 10.

The high voltage transmission circuit 10 and the low voltage transmission circuit 16 are selectively operated by a high voltage transmission signal and a low voltage transmission signal transmitted from the transmission signal generator circuit 9. The receive circuit 11 turns off during the low voltage transmission circuit 16. Further, upon reception of an echo signal, the high voltage switch 40 turns on and the low voltage transmission circuit 16 turns off.

Figure 6:
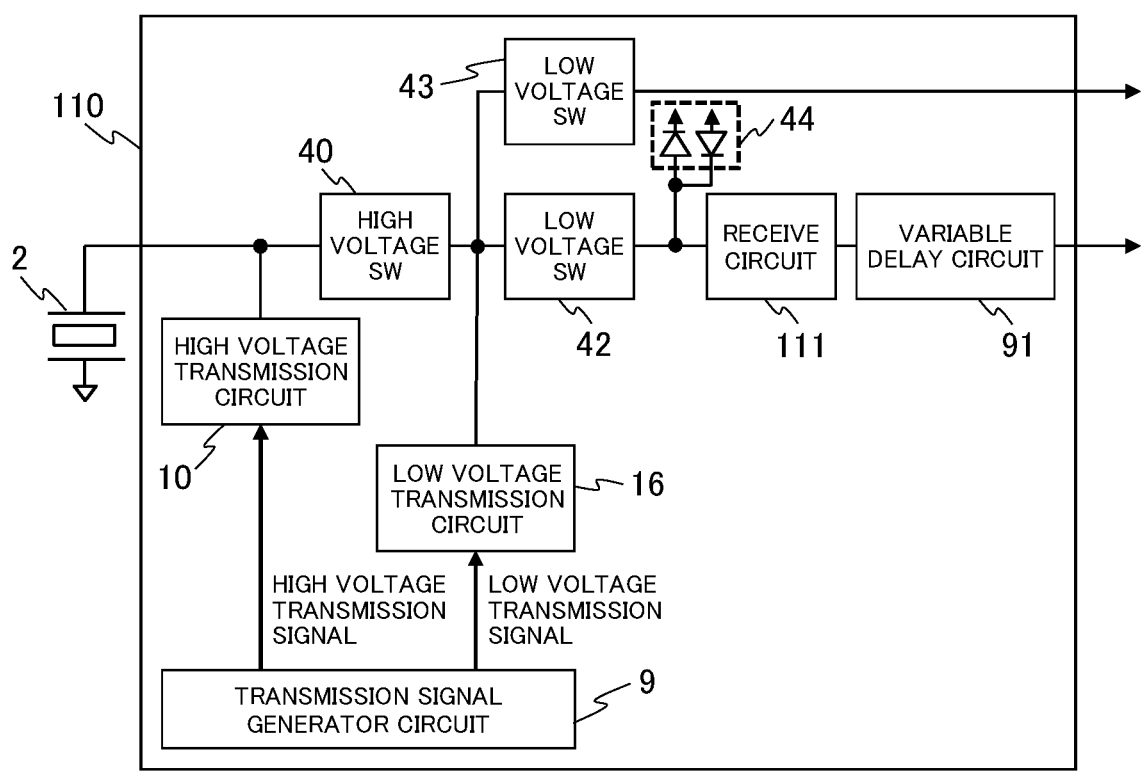
FIG. 6 is a diagram illustrating another example layout in a transducer control unit.

With reference to FIG. 6, another example layout in the transducer control unit 110 is described. In FIG. 6, a low voltage switch 42, a low voltage switch 43, and a clamp diode 44 are added to the layout in FIG. 5. The low voltage switch 42 is disposed between the receive circuit 111 and the high voltage switch 40 and the low voltage transmission circuit 16. The low voltage switch 42 turns on at the time when an echo signal is received, and turns off during the operation of the low voltage transmission circuit 16. The clamp diode 44 is connected between the low voltage switch 42 and the receive circuit 111. The low voltage switch 43 has one end connected between the high voltage switch 40 and the low voltage switch 42, and the other end connected to the output terminal.

The receive circuit 111 can be separated from the low voltage transmission circuit 16 by the low voltage switch 42. Further, the excessive input to the receive circuit 111 can be inhibited by the clamp diode 44. Further, the low voltage switch 43 achieves the output of an echo signal without involving the receive circuit 111.

There may be numerous variations of the embodiments described above. For example, the phrases "relatively low voltage" and "relatively high voltage" used above are not necessarily at several V and 100 V, as long as a "relatively low voltage"<a "relatively high voltage".

REFERENCE SIGNS LIST

1 . . . transmission circuit
2 . . . transducer
3 . . . wiring
9 . . . transmission signal generator circuit
10 . . . high voltage transmission circuit
11 . . . high voltage controller
12 . . . level shifter
13 . . . high voltage driver
14 . . . buffer
15 . . . impedance controller
16 . . . low voltage transmission circuit
17 . . . low voltage controller
18 . . . low voltage driver
20, 26 . . . N-type MOS transistor
21, 27, 28 . . . N-type high voltage MOS transistor
22, 24 . . . P-type MOS transistor
23, 25, 29 . . . P-type high voltage MOS transistor
30, 31 . . . switch
32 . . . resistance
40 . . . high voltage switch
42, 43 . . . low voltage switch
91 . . . variable delay circuit
100 . . . ultrasound diagnostic apparatus
101 . . . main body
102 . . . display
103 . . . controller
104 . . . ultrasonic probe
105 . . . cable 106 . . . control IC
107 . . . transducer unit
110 . . . transducer control unit
111 . . . receive circuit
115 . . . row peripheral circuit
116 . . . column peripheral circuit
117 . . . row control signal
118 . . . column control signal
120 . . . memory
121 . . . setting information

What is claimed is:

1. An ultrasonic probe, comprising:
a high voltage transmission circuit for transmitting a relatively high voltage;
a low voltage transmission circuit for transmitting a relatively low voltage; and
a transducer for selectively receiving a voltage transmitted from the high voltage transmission circuit and the low voltage transmission circuit,
wherein the high voltage transmission circuit includes:
a current source for varying a current generated thereby and a current drawn thereby based on a set signal;
a buffer for driving the transducer in accordance with the currents generated and drawn by the current source; and
an impedance connected to an input terminal and an output terminal of the buffer, the impedance being only a resistance connected parallel to the buffer between the input terminal and the output terminal of the buffer.

2. The ultrasonic probe according to claim 1, wherein the buffer includes an N-type MOS transistor and a P-type MOS transistor, and
when an output resistance of the N-type MOS transistor and the P-type MOS transistor is ro, and an output impedance of the current source is Zout, a resistance value Rzctl of the resistance is in a range of ro≤Rzctl<<Zout.

3. The ultrasonic probe according to claim 1, further comprising
a receive circuit for amplifying an echo signal received by the transducer,
wherein a high voltage switch is installed between (i) the transducer and (ii) the low voltage transmission circuit and the receive circuit, and when the voltage is transmitted from the high voltage transmission circuit, the high voltage switch turns off.

4. The ultrasonic probe according to claim 3, wherein when the voltage is transmitted from the low voltage transmission circuit, the high voltage switch turns on, and the receive circuit turns off.

5. The ultrasonic probe according to claim 3,
wherein a low voltage switch is installed between the receive circuit, the high voltage switch and the low voltage transmission circuit, and
when the voltage is transmitted from the low voltage transmission circuit, the low voltage switch turns off.

6. An ultrasound diagnostic apparatus, comprising the ultrasonic probe according to claim 1.

* * * * *